(12) United States Patent
Filkins et al.

(10) Patent No.: US 10,603,001 B2
(45) Date of Patent: Mar. 31, 2020

(54) ENERGY MODULATED LUMINESCENCE TOMOGRAPHY

(71) Applicants: GENERAL ELECTRIC COMPANY, Schenectady, NY (US); RENSSELAER POLYTECHNIC INSTITUTE, Troy, NY (US)

(72) Inventors: Robert John Filkins, Niskayuna, NY (US); Ahmad Nadeem Ishaque, Clifton Park, NY (US); Alok Mani Srivastava, Schenectady, NY (US); Peter William Lorraine, Schenectady, NY (US); Holly Ann Comanzo, Schenectady, NY (US); Xiaolei Shi, Schenectady, NY (US); Vasile Bogdan Neculaes, Niskayuna, NY (US); Sam Joseph Camardello, Albany, NY (US); Gregory Boverman, Troy, NY (US); Ge Wang, Londonville, NY (US); Wenxiang Cong, Albany, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 882 days.

(21) Appl. No.: 14/789,585

(22) Filed: Jul. 1, 2015

(65) Prior Publication Data

US 2017/0000438 A1    Jan. 5, 2017

(51) Int. Cl.
*A61B 6/00* (2006.01)
*A61B 6/02* (2006.01)
*A61B 8/08* (2006.01)
*A61K 49/00* (2006.01)

(52) U.S. Cl.
CPC ............ *A61B 6/481* (2013.01); *A61B 6/02* (2013.01); *A61B 6/485* (2013.01); *A61B 8/481* (2013.01);
(Continued)

(58) Field of Classification Search
CPC .......... A61B 6/02; A61B 6/481; A61B 6/485; A61B 8/481; A61K 49/0015; A61K 49/0065; C08K 3/08; C09J 11/04
See application file for complete search history.

(56) References Cited

U.S. PATENT DOCUMENTS

2011/0251484 A1    10/2011  Carpenter et al.
2012/0255050 A1    10/2012  Wang
(Continued)

FOREIGN PATENT DOCUMENTS

CN     103239255 A    8/2013
WO    2014006012 A1   1/2014

OTHER PUBLICATIONS

Cong et al., "Stored luminescence computed tomography", International Journal of Engineering and Innovative Technology, Sep. 2013.*

(Continued)

*Primary Examiner* — Christopher L Cook
(74) *Attorney, Agent, or Firm* — Fletcher Yoder, P.C.

(57) ABSTRACT

The present approach generally relates to systems and methods for implementing energy modulated tomographic imaging of nanoparticles. In certain embodiments, a first energy is used to activate probe particles labeling an anatomy or tissue of interest. The probe particles, once activated, emit photons at a different rate and/or spectrum in response to an underlying physiological event, such as action potentials propagating in the labeled anatomy or tissue. The emitted photons may then be detected and used to map or image the occurrence of the physiological event.

14 Claims, 3 Drawing Sheets

(52) U.S. Cl.
CPC ...... *A61K 49/0015* (2013.01); *A61K 49/0065* (2013.01)

(56) References Cited

U.S. PATENT DOCUMENTS

2012/0265050 A1    10/2012  Wang
2015/0119700 A1     4/2015  Liang et al.

OTHER PUBLICATIONS

Ahmad et al., "X-Ray Luminescence and X-Ray Fluorescence Computed Tomography: New Molecular Imaging Modalities", Sep. 4, 2014, IEEE.*

Berry et al. "X-Optogenetics and U-Optogenetics: Feasibility and Possibilities", Photonics, Jan. 7, 2015.*

Yermolayeva et al., "X-ray luminescence of core-shell structured $SiO_2/Lu_2O_3:Eu^{3+}$ and $SiO_2/Lu_2Si_2O_7:Eu^{3+}$ particles", Radiation Measurements, 2011.*

Masserini, "Nanoparticles for Brain Drug Delivery", ISRN Biochemistry, 2013.*

Ueda et al., "Application of FRET probes in the analysis of neuronal plasticity", Front Neural Circuits, Oct. 2013.*

Cong, Wenxiang, et al.; "X-Ray Micro-Modulated Luminescence Tomography (XMLT)"; Opt Express, vol. 22, Issue 5, pp. 5572-5580, Mar. 10, 2014.

Stefanov, Plamen, et al.; "Modulated Luminescence Tomography"; Inverse Problems and Imaging, vol. 9, Issue 2, pp. 579-589, Jan. 28, 2015.

* cited by examiner

ENERGY MODULATED LUMINESCENCE TOMOGRAPHY

BACKGROUND

The subject matter disclosed herein relates to non-invasive imaging techniques, including technique suitable for use in imaging or mapping neurological and/or neuromuscular activity.

The brain consists of functional neuronal and supporting glial cell types that integrate cohesively through mechanical, biochemical, and electrochemical interactions. The function of the brain can be largely ascribed to activities across circuits. These are organized into neural networks in the central nervous system (CNS). Many neurological disease states (e.g., mild and severe cognitive impairment, neuropsychiatric disorders, and traumatic brain injury (TBI)) may be attributed to the dysfunction of neural networks. Indeed, a multitude of neurological disorders have been characterized in which the normal connectivity of neurological circuits is disrupted, giving rise to the observed symptoms. Such disorders include TBI, multiple sclerosis (MS), and stroke, along with toxic-metabolic insults, and infectious/inflammatory disorders.

In addition to the CNS, the peripheral nervous system (PNS) plays a role in normal physiological function and a large number of disease pathologies. In particular, the PNS plays a role in monitoring the state of internal organs and regulating biological responses to infection, injury or other insult. When regulatory processes are inhibited due to injury or illness, peripheral nerve signals can exacerbate a condition, causing pain, inflammation or immune dysfunction. This type of closed loop control architecture raises the possibility that, rather than relying on pharmaceuticals or device interventions, certain conditions may be addressed more effectively by careful modulation of the peripheral nervous system. One prerequisite for modulating the PNS is the mapping and characterization of the structure and function of specific neural circuits. Such mapping and characterization does not currently exist in sufficient detail and existing imaging modalities are not suitable for mapping the activity of neural circuits with sufficient resolution.

BRIEF DESCRIPTION

In one embodiment, a neural activity monitoring system is provided. In accordance with this embodiment, the monitoring system includes an energy delivery mechanism configured to deliver activation energy to a measurement volume when a set of nanoparticles are present within the measurement volume. The nanoparticles emit photons when activated by the external energy source and, once in an activated state, further emit a pulse of photons in response to a physiological event when such a physiological event occurs within the measurement volume. The monitoring system also includes one of more photodetectors configured to detect photons emitted by the nanoparticles in response to the physiological event and a data acquisition system configured to read out signals generated by the one or more photodetectors in response to the detected photons. The monitoring system further includes an image reconstructor or a signal analyzer, and event recorder configured to reconstruct one or more images and/or features of a nanoparticle distribution, time domain activity, and temporal relationship among measured signals and biological events derived from these measurements and energy excitation parameters.

In a further embodiment, an energy modulated tomographic imaging method is provided. In accordance with this method, an external energy source is used to activate a plurality of functionalized nanoparticles within a region of interest. The activated nanoparticles emit photons at a background rate when not further stimulated by an underlying tissue and at one or both of a different rate or energy when further stimulated by action potentials or field potentials associated with the underlying tissue. The photons emitted by the plurality of functionalized nanoparticles are detected. One or more of a multi-dimensional image, a time-domain activity representation, or a representation of temporal relationship between the detected photons and biological features is generated based upon the photons emitted at the different rate or energy (spectrum).

In an additional embodiment, an X-ray modulated tomographic method is provided. In accordance with this method an X-ray beam that is one or both of focused or micro-modulated is directed at a tissue-of-interest labeled with functionalized nanophosphors to activate the functionalized nanophosphors to emit at a background luminescence when not further stimulated. Photons emitted by the functionalized nanophosphors when further stimulated by action potentials or local field potentials associated with the labeled tissue of interest are detected. One or more of a multi-dimensional image, a time-domain activity representation, or a representation of temporal relationship between the detected photons and biological features are generated based upon the detected photons.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
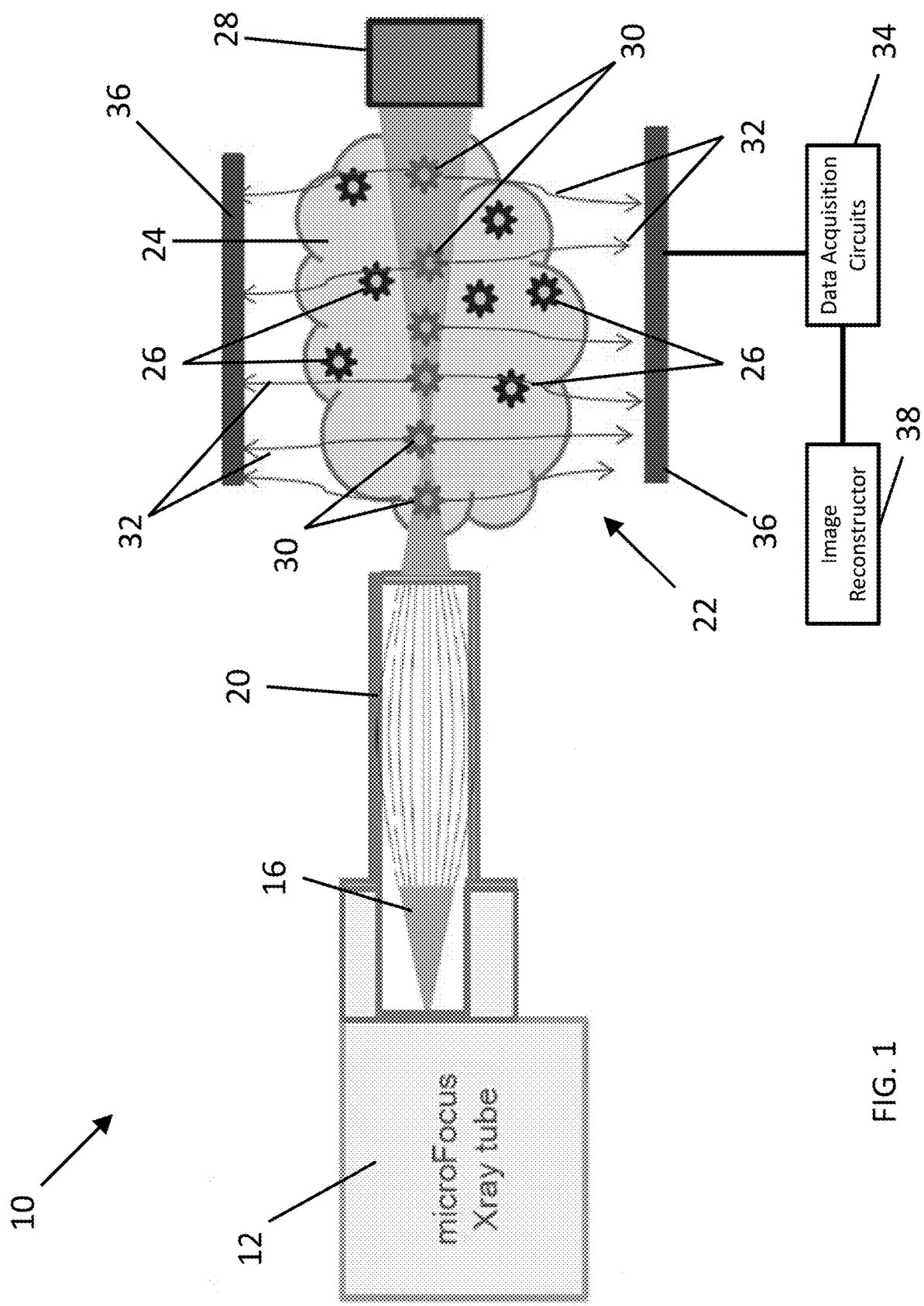
FIG. 1 depicts one example of an embodiment of a modulated luminescence tomography imaging system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As discussed herein, for various clinical, diagnostic, and research applications, conventional neural imaging approaches may be unsatisfactory for a variety of reasons. Using conventional approaches, it is generally not possible to generate internal images of the body having microscopic resolution or which depict neural or neuromuscular electrical activity in a useful manner. In accordance with the present discussion, these limitations may be overcome, allowing representations (e.g., images, maps, or other suitable representations) to be generated that correspond to electrochemical and electrophysiological events within the body, such as events related to the activity of individual or collective CNS or PNS circuits. Further, the present approach allows for the monitoring of time-domain neural activity within a tissue of interest and allows for temporal relationships to be monitored and/or viewed between the measured signals, typically in the context of the underlying biological features of interest. Thus, the present approach may allow functional maps of neuronal communications (e.g., neuronal networks, neural circuits, and so forth) to be generated, analyzed, and/or viewed. The present approach, therefore, is suitable for analyzing the brain as well as central or peripheral nerve tissues. By way of example, and as discussed herein, the present techniques may be suitable for imaging cortical networks intact through the skull.

Certain of the present embodiments relate to the use of a tomographic imaging modality that is based on principles that fundamentally couple X-ray and optical imaging techniques via use of a functionalized nanophosphor intermediary that scintillates in the presence of X-rays. In particular, the present techniques may be characterized as X-ray driven, functional microscopy approaches in which X-rays are used to activate or excite functionalized nanophosphor probe molecules selectively attached or proximate (e.g. within the proximate extracellular spaces) to target tissues within a volume of interest. These approaches, known herein as X-ray micro-modulated luminescence tomography (XMLT) are suitable for in vivo high-resolution cellular imaging, including imaging of neurological tissue. In turn, the imaging context may be monitored or analyzed over time to obtain spatial- and time-domain information that may be used in assessing or determining functional mappings of neural activity.

The XMLT approach discussed herein offers several advantages over conventional approaches. In particular, the present techniques provide a variety of advantages including, but not limited to: the ability to achieve resolution that is less than or equal to 20 microns (e.g., 5-20 microns, 5-10 microns, and so forth), the ability to observe single cells (i.e., single cell resolution), the ability to acquire structural and molecular data, and the ability to observe neural and neuromuscular circuits in action (i.e., voltage and/or action potential sensitivity).

It should be appreciated that, though X-ray stimulation is discussed herein as an example, other energy delivery mechanisms may also be employed in addition to or instead of X-rays to initially excite or activate the probe particles as part of the imaging process. For example, delivery of ultrasound energy and/or heat (i.e., thermal energy) applied at a site undergoing imaging may also be used to activate probe particles, as discussed herein, and may used in an imaging operation in which ultrasound or thermal energy is instead to provide the initial probe particle activation energy.

Figure 2:
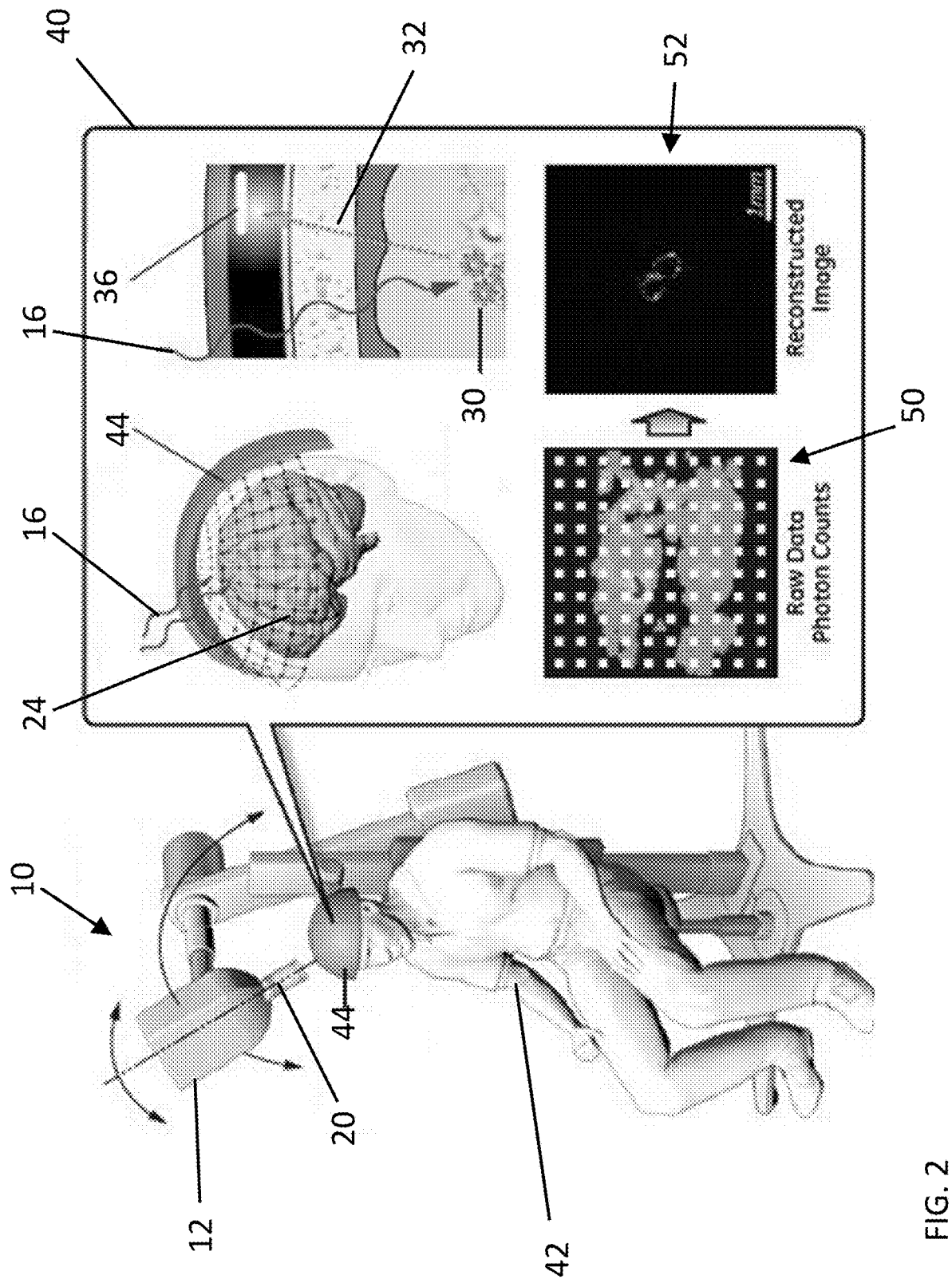
FIG. 2 depicts a process flow of image reconstruction steps in conjunction with a further example of a modulated luminescence tomography imaging system, in accordance with aspects of the present disclosure.

With the preceding discussion in mind, FIG. 1 depicts a schematic view of an imaging system suitable for performing X-ray micro-modulated luminescence tomography. FIG. 2 depicts an example of a physical implementation in conjunction with a stylized process flow of different steps in image generation.

As shown in FIG. 1, an imaging system 10 includes an X-ray source 12 (e.g., a microfocus X-ray tube) configured to emit a beam 16 of X-rays toward an imaging region 22. In the depicted example, beam 16 of X-rays is focused using a focusing element (e.g., a polycapillary focusing element 20, X-ray grating and zone-plate, and so forth) suitable for focusing, constraining, or otherwise limiting the extent of beam 12 as it travels through the imaging volume. In embodiments employing a polycapillary lens 20, a dual-cone X-ray beam geometry results, facilitating the fine focus contemplated herein. In certain embodiments, the X-rays may be micro-modulated, such as by control signals generated by an X-ray controller or by manipulation of the focusing and/or emission elements, in addition to, or in place of the applied focus. The X-rays 16 are directed toward an imaging volume 22. In the depicted example, a region of tissue 24 (e.g., neural or brain tissue) is present in the imaging volume 22. In one implementation, a portion of the beam 16 of X-rays pass through the tissue 24 and are stopped by a beam blocking or absorbing structure 28. In other implementations, no beam blocker 28 may be explicitly provided.

In the depicted example, portions of the tissue 24 (e.g., axons) are labeled with functionalized nanophosphor particles 26. More generally, the labeled tissue 24 may be a region of interest within a patient, an animal, or in other contexts, such as an engineered tissue construct (e.g., an organoid). When exposed to the narrowly focused and/or micro-modulated beam 16 of X-rays, some portion 30 of the nanophosphor particles 26 are energized to an excited or activated state (e.g., a persistently luminescent state in which a background luminescence is maintained). In particular, the activated nanophosphor particles 30 emit photons 32 at a characteristic rate and/or wavelength, typically in the optical or near infrared wavelengths. The photons 32 may in turn be detected by photodetectors 36 (e.g., an electron multiplying charge coupled device (EMCCD)) array or camera) provided over some angular range about the imaging region 22 (here shown as a cross section of a cylindrical arrangement), allowing data to be collected over this angular range, such as via one or more data acquisition circuits or subsystems 34 configured to readout the photodetectors 36. In some embodiments the data acquisition circuits or systems 34 perform some degree of initial processing of the read-out signals, such as analog-to-digital conversion, bad pixel correction, gain correction, and so forth. The read-out signals may be subsequently provided to an image reconstructor and/or event recorder circuit or subsystem 38 which processes the signals, as discussed herein to generate a representation, (e.g., a two- or three-dimensional image, a mapping representation, a time domain activity representation, and so forth) showing nanoparticle distribution and/or nanoparticle activity (e.g., photon emissions) over time within the imaged volume and/or the temporal relationship among the measured signals (i.e., detected photons) and biological features.

As noted above, in some embodiments, the nanophosphor particles 30, once excited, are persistently luminescent for some interval of time. In such a persistently luminescent state, the activated nanophosphor particles, which maintain a persistent or background luminescence, may respond to proximate physiological processes by flashing or otherwise emitting additional photons 32 at a characteristic wavelength. For example, the activated nanophosphor particles 30 may emit photons 32 in response to an action potential of a single labeled neuron, a field potential of an ensemble or aggregate of proximate neurons, or other electrical events associated with the labeled tissue. In response to such additional stimulation by the physiological process of interest, the nanophosphor particles may emit photons at a different (e.g., elevated) rate and/or different spectrum than what is associate with the background luminescence associated with activation alone. In this manner, detected photons 32, and images generated using photons 32, may be indicative of a selected biological phenomena, such as the depolarization events associated with neural or neuromuscular activity. When aggregated and analyzed over a period of time, this information may, therefore, be useful in mapping functional networks of neural activity.

By way of example, the firing of a neuron is typically associated with a cascaded response in which sodium channels within the neuron open and close in a propagating manner along the neuron length, followed by the opening and closing of potassium channels. As a consequence of this ion exchange activity (i.e., depolarization), an action potential may propagate along the firing neuron, starting and ending at approximately −70 mV but peaking at approximately +30 mV at the time when sodium channels are closing and potassium channels are opening at a given location on the neuron. This propagating action potential may give rise to a high, neuron-derived, electrical field on the order of 100 mV/10 nm→10 MV/m that propagates along the firing neuron. Nanophosphor particles that label such a neuron, when exposed to such an electrical field during firing of the neuron, may experience electron-hole recombination, resulting in the emission of photons 32 at a characteristic wavelength (e.g., optical or near infrared wavelengths) for the nanophosphor in question. These generated photons 32 can be detected and used to generate images that allow visualization of the action potentials associated with the labeled neurons.

An example of one possible implementation of such a system 10 is shown in FIG. 2, which also depicts a process flow (window 40) of associated steps demonstrating aspects of an imaging session as discussed herein. With respect to the imaging system 10, FIG. 2 shows an arrangement in which the X-ray source is mounted on a movable arm, allowing angular motion (e.g. rotation) of the X-ray source 12 about two-axes spanning an imaging volume in which the head of a patient 42 has been positioned. In the depicted example, the photodetectors 36 are located in a helmet 44 positioned on the head of the patient 42.

As shown in the sequence of images presented in the process flow, X-ray radiation 16 from the source 12 penetrates the helmet 44 and is narrowly focused on a region of interest, here within the brain. Portions of the tissue within the region of interest are labeled with one or more types of functionalized nanophosphor particles, which may be activated or excited (e.g., activated nanophosphor particles 30) in the presence of the X-rays 16 to a persistently luminescent state. In the depicted example, the activated nanophosphor particles 30 are associated with an axon of a neuron within the brain. Depolarization of the axon when firing creates a propagating electrical field of sufficient density to induce emission of photons 32 from the activated nanophosphor particles 30 at a characteristic wavelength. Alternatively, a field potential generated by multiple neurons whose membranes depolarize in proximity to one another may generate a field potential sufficient to further stimulate nanophosphor particles 30 even when such particles do not directly label the depolarizing axons in question. The photons 32 induced by such action potentials or field potentials may be detected at the photodetectors 35, which may determine a line-of-flight for each respective photon and may aggregate the detected photons 32 as photon counts 50. These photon counts 50 and the corresponding line-of-flight information may be reconstructed to generate an image 52 that depicts structural (e.g. brain structure) and/or functional (e.g., membrane potentials) characteristics of the patient within the imaged region. When aggregated over an interval of time, the combined spatial and temporal data points may provide useful functional data that allows neural networks and/or circuits to be mapped or evaluated.

With the preceding generalized discussion in mind, certain additional details of the X-ray stimulation, the functionalized nanophosphors, and tomographic image reconstruction are provided below which may be relevant to certain envisioned implementations.

X-Ray Excitation

With respect to X-ray based system, such as those described above, X-rays offer certain advantages over other excitation mechanisms, including the ability to penetrate deeply into tissue and the ability to maintain a small excitation volume. This approach provides several merits including, but not limited to: (1) penetration through a variety of tissues, including bone, to probe neuronal bundles, (2) excitation of nanoparticles (e.g., nanophosphors) for a suitable flux of optical photons, and (3) higher X-ray energy (i.e., shorter wavelengths, such as those in the picometer range) focusing into a smaller spot size in the tissue. By enabling such improved focus capabilities, voxel size may be reduced along with X-ray tube power requirements. Further, X-ray energy spectra may be selected and employed that provide low scattering and the use of X-rays may allow voxels to be resolved with dimensions less than 100 microns on a side. In certain embodiments, 50 keV to 60 keV X-ray energy may be employed such that the absorption-contrasts between the tissue (which is largely water) and nanoparticle matrix (e.g., doped $Lu_2O_3$) is maximized.

Functionalized Nanophosphors

With regard to the use of functionalized nanophosphors, cell-specific imaging may be achieved by functionalizing nanophosphor particles (e.g., nanoscale particles of a material that scintillates when exposed to X-ray radiation) with surface coatings that bind to specific cellular proteins (i.e., cellular markers and/or extracellular features of interest). In certain embodiments the nanophosphor probe molecules may take the form of one or more functionalized nanophosphor dyes suitable for labeling anatomic structures such as neurons or nerve bundles. Thus, in such embodiments, functionalizing the nanophosphor dye may involve providing a surface coating on the dye that promotes binding to axons (e.g., to surface proteins distinct to axons).

In certain embodiments, the functionalized nanophosphors can be delivered to a target site by injection (e.g., intravenously), by catheter (e.g., intravascularly or as part of a catheter-based interventional procedure), by topical administration (such as in a surgical procedure), via the cerebrospinal fluid, or by other suitable administration mechanisms. Further, in certain embodiments, subsequent to administration and examination, the functionalized nanophosphors may be cleared through the kidneys or via other bodily processes that typically filter and remove administered agents.

In certain implementations, one or more types of functionalized nanophosphor particles may be employed, such as nanophosphor particles functionalized to have different tissue type selectivity and/or having different characteristic photon emission frequencies. In such a scenario, resulting images may depict the photon emission from the different probes, each of which may convey different structural and/or functional information. Alternatively, a given set of functionalized nanophosphors may be subjected to multiple doping operations so as to emit photons at more than one characteristic rate or wavelength, depending on the type and/or extent of stimulation. In such a scenario, different structural and/or functional information may be obtained using the same nanophosphors.

In certain embodiments, as discussed herein, even if it is not feasible to label a neuronal compartment directly to detect individual depolarizing events or action potentials, it is possible to target the functionalized nanophospor particles to an extracellular location where the local field potential associated with a depolarization event will vary based on summed signal from the simultaneous activity of an ensemble or aggregation of neurons to an extent sufficient to induce photon emission. That is, the nanophosphor particles, being voltage sensitive, will respond to this voltage change. In such an embodiment, instead of measuring the activity of a single neuron, the activity of an ensemble of neurons is instead measured.

Suitable inorganic functionalized nanophosphors will typically be electroluminescent, non-toxic, photo-stable, non-blinking, tunable, (by selective doping), and may even be customized to emit at multiple wavelengths (by multiple selective doping operations). In addition, functionalized nanophosphors may be selected and/or tuned so as to maximize or optimize the power delivered to the probe particles, as opposed to the patient tissue. Luminescent persistence may also be tuned, from nano- to milliseconds, so as to achieve read times suitable for a given application. The functionalized nanophosphors can be fabricated using known techniques at the nano-scale (e.g., less than 30 nm) without changing the luminescent properties of the nanophosphors.

In certain embodiments, where the nanophosphors employed are excited by X-rays, it may be desirable that the underlying lattice of the nanophosphor particles have a high physical density and contain a large proportion of elements with a high atomic number (e.g., a Z-number greater than 42 or 72) in order to stop the highly penetrating radiation in the relatively short distances typically available. Examples of two possible candidates of suitable scintillating nanophosphor materials are based on $Lu_2O_3$, which has a physical density of 9.42 g/cm$^3$. The first example is $Lu_2O_3:Eu^{3+}$, which emits at 610 nm when excited. The second example is $Lu_2O_3:Yb^{3+}$, which emits in the infrared spectrum at approximately 1,000 nm (thus allowing deeper penetration of the emitted photons through biological tissues).

As noted above, in practice the nanophosphor scintillator material may be excited by exposure to X-rays, such as to a state of persistent luminescence. When in this excited state, the nanophosphor material may respond to an environmental stimulus (e.g., voltage, pH, heat, elastic waves, and so forth) by emitting photons 32. In certain embodiments, the functionalized nanophosphors may be selected or designed so as to emit at a different rate or wavelength when stimulated by a physiological process than when merely in an activated or excited state (i.e., the background luminescence may differ from the rate and/or wavelength of photon emission when further stimulated by a physiological process of interest). However, in other embodiments, the photon emission in response to the physiological process of interest is at the same wavelength as the background luminescence and the characteristics of interest is the increase in photon emissions that coincide with the occurrence of the physiological process.

Thus, in one implementation, excited nanophosphor particles may respond to electrical pulses generated by membrane action potentials, or by field potentials generated in response to the activity of multiple proximate axons, by flashing (i.e., emitting photons 32) at a known wavelength in synchrony with the action potential. The persistent decay of the nanophosphor is then modulated by neuronal firing. As discussed herein, these neuronal firing signals can be read out by photodetectors 36 (e.g., as embodied in a sensitive, high frame rate camera) and unmixed to generate images that map network connectivity of specific nerve systems. In this manner, signal propagation along a labeled axon or circuits composed of such labeled axons can be visualized and connectivity at the level of individual neurons, such as in the neocortex, may be mapped.

Optical Detection

In certain implementations it is estimated that the nanophospor particles, as discussed herein, can generate approximately 20 photons per keV of absorbed X-ray energy. With this in mind, in one example a sample of nanophosphors at pico-molar concentration, irradiated with quasi-monochromatic 50 mGy dose at 60 keV would generate 109 near infrared (~1,000 nm wavelength) photons per mm$^3$. Thus, the photodetectors 36 (e.g., photodiodes) selected and the geometric placement of such photodetectors 36 should be suitable for detecting such a quantity of photons, of distinguishing between different photon detection events, and of calculating a line of flight for detected photons with sufficient certainty. With this in mind, in one embodiment, the optical detection design is implemented as an integrating sphere (or hemi-sphere), as shown in FIG. 2. Alternatively, optical detection may be accomplished with a curved array of photodetectors, such as employing a curved glass substrate(s) and photodetector materials.

As will be appreciated, variations in light propagation of the photons 32 to the surface may influence the measurements made at the photodetector 36. For example, an area that is optically shadowed by an anatomical feature will appear darker than other areas having clearer paths to the surface and to the photodetectors 36. Therefore, compensation for diffuse optical propagation may be employed for imaging a large extended feature with widely distributed nanophosphor particles. However, such compensation may not be needed for smaller target volumes, such as peripheral nerves. Indeed, for peripheral nerves, the number of X-ray views, dosage, and acquisition time will be comparatively small and resolution will be superior.

Image Reconstruction

As described above, luminescence data (i.e., photons 32) is collected, processed, calibrated, and mapped onto a structural model of an object under study, such as a structural image derived using a second imaging modality. In one implementation, a radiative transfer model and compressive sensing (CS) based algorithm is employed to reconstruct a three-dimensional (3D) distribution of nanophosphors based on the detected photons 32.

Such an approach may employ a dual-cone transform for image reconstruction. In particular, the X-ray illumination is not a point in space but fills a cone pointing to the focus and away. In the vicinity of the nerve fiber, the X-ray intensity will look like a cylinder with a narrow waist. Resolution is improved by looking at the target nerve fiber (or other tissue of interest) from a variety of angles, so the extended size of the 3D X-ray focal volume can be deconvolved. This is a form of tomography and compressed sensing concepts may be used to minimize the number of views required as well as dose and acquisition time.

As noted above, one aspect of the present approach is the possibility of analyzing or monitoring the acquired nanoparticle spatial distribution and activity (i.e., photon emissions) over time (e.g., in the time domain) to derive additional functional data of interest. In particular, by analyzing or monitoring the non-background photon emissions over time and by being able to localize such emissions in a spatial context, it is possible to determine (and monitor or view) networks or circuits of neural activity that may be of interest within the imaged tissue. In this manner, functional maps of neuronal communication may be established, monitored, viewed, and so forth. Such maps may then be compared to known or established functional mappings for diagnostic or research purposes, may be used to characterize baseline or normal neuronal behavior, or may be used to characterize abnormal behavior associated with an established disorder.

Example: Peripheral Nerve Structure Imaging

The following example describes an approach that may be used to acquire high resolution spatial maps of peripheral nerve structures. The concept may be described qualitatively as follows: In the case of a nerve fiber that has functionalized nanophosphor particles attached to the cell membrane, a focused X-ray beam is scanned across the nerve fiber, exciting the nanophosphor particles. In this example, light is emitted from the known location of the X-ray focus and propagates diffusively to a photodetector 36, where the measured amplitude approximates the density of phosphor particles at the focus. The signals corresponding to the measured photons 32 are processed to produce localized action potential measurements or combined to produce higher resolution spatial images, as described above.

Figures 3, 4:
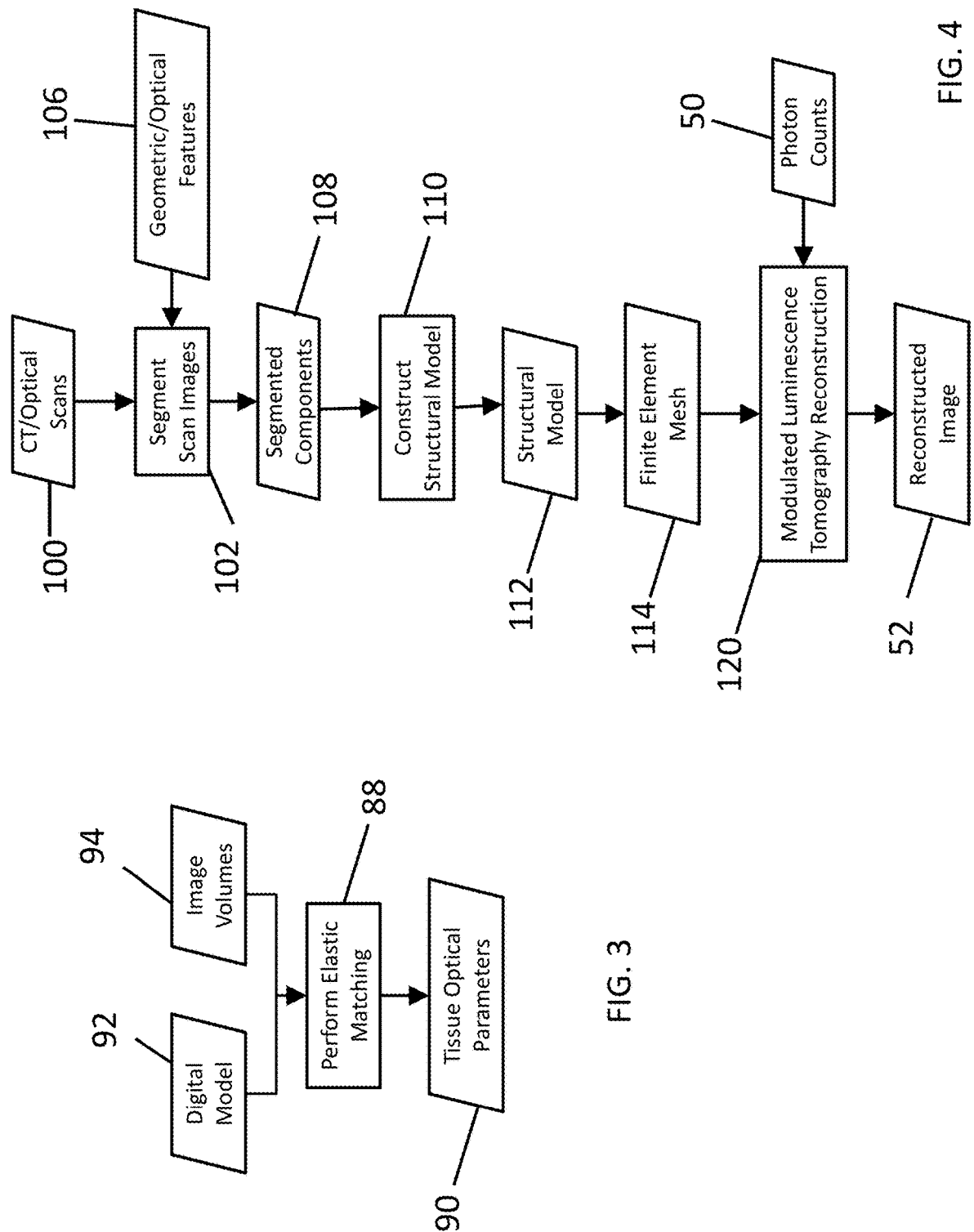
FIG. 3 depicts a process flow illustrating possible steps in determining tissue optical parameters, in accordance with aspects of the present disclosure.
FIG. 4 depicts a process flow illustrating possible steps in reconstructing an image in accordance with aspects of the present disclosure.

As part of this example, and turning to FIG. 3, in a numerical simulation, tissue optical parameters 90 are obtained via elastic matching (block 88) of a digital model 92 (with both anatomical and optical properties) to various small animal image volumes 94. With respect to the physical experiments, and turning to FIG. 4, from individualized CT and optical scans 100, each physical phantom or ex vivo sample is segmented (block 102) into major components 108 in terms of geometrical and optical features 106. Using computer graphics techniques (Amira 4.0, Mercury Computer Systems, Inc. Chelmsford, Mass.), a structural model 112 is constructed (block 110) from segmented results, and a finite-element mesh 114 of tetrahedrons is generated. This model 114 will serve as prior knowledge for modulated luminescence tomography (MLT) reconstruction (block 120) of an image 52. The tetrahedron-based inhomogeneous Monte-Carlo optical simulator (TIM-OS) supports highly complex tissues. TIM-OS can be implemented on a processor-based system and can serve as a forward solver for iterative MLT reconstruction.

With respect to the imaging model, it may be assumed that $X(r)(r \in \Omega)$ is the X-ray intensity distribution applied to excite nanophosphors in an object for persistent luminescence emission. The induced luminescence energy in the nanophosphors is proportional to the nanophosphor concentration $\rho(r)$ and the energy storage yield $\eta$ of the nanophosphors, which is the quantum yield per unit nanophosphor concentration. The luminescence signals will decay exponentially at a rate $\alpha$, which can be considered as a constant in certain implementations, and can be expressed as $$s(r,t) = \alpha \eta X(r) \rho(r) \exp(-\alpha t), r \in \Omega. \quad (1)$$

The emitted light propagation involves absorption and scattering in a biological tissue. This process is described by the radiative transport equation (RTE). Based on the RTE model, photon flux rates on an external surface in an exposure interval $[t_{k-1}, t_k]$ can be expressed in terms of a Green function:

$$\Phi(r, t_k) \int_\Omega G(r, r') S(r', t_k) dr', \quad r \in \Omega, \quad (2)$$

where r is a positional vector, $\Phi(r,t_k)$ is the fluence rate at r and $S(r,t_k)$ the intensity of light sources from nanoparticles is given by:

$$S(r,t_k) = \int_{t_{k-1}}^{t_k} s(r,t) dt = \eta X(r) \rho(r) [\exp(-\alpha t_{k-1}) - \exp(-\alpha t_k)]. \quad (3)$$

In certain embodiments of the imaging system 10, an X-ray lens (e.g., polycapillary focusing element 20) may be positioned in front of the X-ray source 16 to bend the output beams 16 towards a focal spot, forming double cones with their shared vertex point inside the tissue. The polycapillary lens 20 delivers much more X-ray energy around the converging point. For biological soft tissues, an X-ray intensity distribution in the dual cones is calculated with inverse squared distance weighting, $$X(r) = I_0 \frac{W(r, r_0)}{\|r - r_0\|^2}, \quad (4)$$

where $r_0$ is the vertex of the two cones, $I_0$ is the intensity of the x-ray source, and $W(r,r_0)$ is the aperture function of the twin cones at the vertex. The data acquired by an electron multiplying charge coupled device (EMCCD) camera or a similar, photo-sensitive detector highlights the light emission around the vertex. In one such embodiment, all the luminescence data are integrated into a single reading:

$$\int\int_{S^2}\int \Phi(r, t_k) dr = I_0 \int_\Omega \left[ \int\int_{S^2}\int G(r, r') \frac{W(r', r_0)}{\|r' - r_0\|^2} Q(r', k) dr \right] dr', \quad (5)$$

where $Q(r) = \eta \rho(r)[\exp(-\alpha t_{k-1}) - \exp(-\alpha t_k)]$ and $S(r, t_k) = X(r) Q(r)$.

To generate a sufficient amount of data for image reconstruction, the focal point of the dual cones of X-rays is scanned over all the grid points in a region of interest (ROI). Then, the integral equation (5) can be discretized into a linear system of equations, which is diagonal dominant due to performing a point-wise scanning of micro-focusing X-rays, and has a well-posed solution for MLT, which leads to image reconstruction. A low-rank seeking method may be employed to reconstruct an underlying nanophosphor distribution and unmix signals from neuron firing patterns. Specifically, this approach targets an optimal set of image domain transformations such that the transformed images can be most effectively decomposed into the sum of a sparse tensor of errors and a low-rank tensor characteristic of recovered images. This optimization problem can be reduced to a sequence of convex programs to minimize the sum of $l_p$-norm and nuclear norm of the two component tensors, which can be solved by scalable convex optimization techniques with at a fast converging rate.

As noted herein, the disclosed approaches may be suitable for discerning neuron firing patterns in certain embodiments. For example, time-gated and spectrally-resolved data acquisitions in the regions-of-interest may be employed. From the resultant data, both the distribution and dynamics of the nanophosphors and firing patterns can be estimated. The signal variation of nanophosphors allows observation of reorganization and dynamics of transmembrane molecules, such as may be associated with membrane depolarization events. Firing patterns may be discerned and reveal cellular communications in a direct and large-scale manner. With the intrinsic correlation across image frames between multiple time gates and spectral channels, these images form a low rank tensor, which can be utilized to improve image quality significantly.

In practice, due to the time required to acquire all necessary views and the photon flux per unit time being distributed over many spatial locations, it may be useful to trade, to a certain degree, spatial resolution for signal-noise-ratio (SNR) or vice versa. Once a time-varying signal is reconstructed for each relatively large voxel in a region-of-interest, an un-mixing approach may be employed to extract rich information on neuron firing patterns.

The neuron firing generates a characteristic wave form, which may be expressed by wavelet base functions. Wavelet analysis may be employed for unmixing in this context. From the experimental data, the neuron firing patterns, once superimposed onto luminescence signals, can be expressed as $$L(r, t) = N(r) + \sum_{m,n} c_{m,n} W_{m,n}(r, t) \qquad (6)$$

where the first term in the right hand side of Eq. (6) is the natural decay of stored energy, and the second term is the stimulating contributions from neuron firings.

Based on the Beer-Lambert law:

$$S(r,t_e) = E(r)[\exp(-\tau \int_0^{t_s} L(r,t)dt) - \exp(-\tau \int_0^{t_e} L(r,t)dt)] \qquad (7)$$

where $E(r) = \eta X(r)\rho(r)$, and $\tau$ is the light emission efficiency from stimulating. Furthermore, from the reconstructed time-resolved source emission distribution $S(r,t_1)$, $S(r,t_2)$, ..., $S(r,t_m)$ in a region-of-interest obtained by the methodology described above, the following unmixing system may be derived:

$$\begin{cases} \tau \int_0^{t_1} L(r, t) dt = -\log[1 - S(r, t_1)/E(r)] \\ \tau \int_0^{t_2} L(r, t) dt = -\log[1 - (S(r, t_1) + S(r, t_2))/E(r)] \\ \vdots \\ \tau \int_0^{t_m} L(r, t) dt = -\log[1 - (S(r, t_1) + S(r, t_2) + \ldots + S(r, t_m))/E(r)] \end{cases} \qquad (8)$$

This system can be solved using an iterative method to obtain both the nanophosphor concentration $\rho(r)$ and wavelet coefficients $\{c_{m,n}\}$ of firing patterns described in Eq. (6). Also, this solution can be regularized using the database of independently recoded neuron firing patterns to improve the unmixing quality, in terms of amplitudes, frequencies, periods, and other features of the neuron firing patterns. Furthermore, the intrinsic correlation across image frames at multiple time gates can be utilized to improve the unmixing quality further in the PRISM framework.

Technical effects of the invention include generating dynamic images or maps illustrating action potentials of neural or neuromuscular tissue. Further technical effects include voltage- and/or potential-sensitive imaging of any tissue exhibiting action potentials.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An energy modulated tomographic imaging method, comprising:
using an external energy source, activating a plurality of functionalized nanoparticles within a region of interest to a state of persistent background luminescence for a period of time, wherein the activated nanoparticles emit photons at a background rate when not further stimulated by an underlying tissue and at one or both of a different non-background rate or energy when further stimulated by action potentials or field potentials associated with the underlying tissue;
detecting, during the state of persistent background luminescence, the photons emitted by the plurality of functionalized nanoparticles; and
generating one or more of a multi-dimensional image, a time-domain activity representation, or a representation of temporal relationship between the detected photons and biological features based upon the photons emitted at the different non-background rate or energy, wherein the biological features comprise neural activity.

2. The energy modulated tomographic imaging method of claim 1, wherein the region of interest comprises a patient, an animal, or an organoid.

3. The energy modulated tomographic imaging method of claim 1, wherein the temporal relationship between the detected photons and biological features corresponds to functional map of neuronal communication.

4. The energy modulated tomographic imaging method of claim 1, wherein activating the plurality of functionalized nanoparticles comprises exposing the plurality of functionalized probe particles to a focused and/or micro-modulated X-ray beam.

5. The energy modulated tomographic imaging method of claim 1, wherein activating the plurality of functionalized nanoparticles comprises exposing the plurality of functionalized nanoparticles to thermal or ultrasonic energy.

6. The energy modulated tomographic imaging method of claim 1, wherein the plurality of functionalized nanoparticles comprise nanophosphor particles functionalized to label central nervous system or neuromuscular tissue.

7. The energy modulated tomographic imaging method of claim 1, wherein the plurality of functionalized nanoparticles comprise functionalized particles of doped $Lu_2O_3$.

8. The energy modulated tomographic imaging method of claim 1, further comprising administering the plurality of functionalized nanoparticles to label the underlying tissue.

9. The energy modulated tomographic method of claim 8, wherein the plurality of functionalized nanoparticles are administered by at least one of: intravenous administration, catheter-based delivery, topical administration, and via the cerebrospinal fluid.

10. The energy modulated tomographic imaging method of claim 1, wherein generating the multi-dimensional image comprises mapping luminescence data to a structural model of an anatomic region undergoing evaluation.

11. An X-ray modulated tomographic method, comprising:
  directing an X-ray beam that is one or both of focused or micro-modulated at a tissue-of-interest labeled with functionalized nanophosphors to activate the functionalized nanophosphors to emit background photons at a state of persistent background luminescence for a period of time when not further stimulated;
  detecting, during the state of persistent background luminescence, non-background photons emitted by the functionalized nanophosphors when further stimulated by action potentials or local field potentials associated with the labeled tissue of interest, wherein the non-background photons are associated with at least one of: a non-background rate or energy, different from a corresponding background rate or energy associated with the background photons; and
  generating one or more of a multi-dimensional image, a time-domain activity representation, or a representation of temporal relationship between the detected photons and biological features based upon the detected photons, wherein the biological features comprise neural activity.

12. The X-ray modulated tomographic method of claim 11, wherein the X-ray beam is at an energy of 50 keV to 60 keV.

13. The X-ray modulated tomographic method of claim 11, wherein the functionalized nanophosphors comprise a matrix of $Lu_2O_3$.

14. The X-ray modulated tomographic imaging method of claim 11, wherein the functionalized nanophosphors have a diameter less than 30 nm.

* * * * *